United States Patent [19]
Cross et al.

[11] Patent Number: 5,372,818
[45] Date of Patent: Dec. 13, 1994

[54] METHOD OF TREATING FESCUE TOXICOSIS WITH DOMPERIDONE

[75] Inventors: Dee L. Cross, Central, S.C.; James R. Strickland, Knoxville, Tenn.

[73] Assignee: Clemson University, Clemson, S.C.

[21] Appl. No.: 12,296

[22] Filed: Feb. 1, 1993

[51] Int. Cl.$^5$ .............................................. A23K 1/165
[52] U.S. Cl. ................................... 424/442; 514/276; 514/450
[58] Field of Search ................... 424/442; 514/450, 276

[56] References Cited

U.S. PATENT DOCUMENTS

| | | | |
|---|---|---|---|
| 4,066,772 | 1/1978 | Vandenberk et al. | |
| 4,755,519 | 7/1988 | Dougherty et al. | 514/276 |
| 4,847,243 | 7/1989 | Wallace | 514/450 |
| 4,880,632 | 11/1989 | Lipham et al. | 424/442 |

OTHER PUBLICATIONS

Drug Facts and Comparisons, 1991 Edition, A Division of J. B. Lippincott Company pertinent p. 2561.

Effects of Domperidone and Thyrotropin-Releasing Hormone on Secretion of Luteinizing Hormone and Prolactin During the Luteal Phase and Following Induction of Luteal Regression in Sheep, D. R. Deaver et al., Domestic Animal Endocrinology, vo. 4(2):95–102, 1987.

"Notice of Drug Shipment" forms relative to domperidone for fescue toxicosis in horses, Dee L. Cross, Division of Agriculture and Natural Resources, Clemson University, Jun. 8, 1993.

Domperidone, A Specific In Vitro Dopamine Antagonist, Devoid of In Vivo Central Depaminergic Activity, Pierre M. Laduron et al., Biochemical Pharmacology vol. 28, pp. 2161–2165, Janssen Pharmaceutica, B-2340 Beerse, Belgium.

Minireview, The Substituted Benzamides—A novel Class of Dopamine Antagonists, P. Jenner et al., Life Sciences, vol. 25, pp. 479–486, Institute of Psychiatry & King's College Hospital Medical School, Denmark Hill, London SE5, UK.

*Primary Examiner*—Paul R. Michl
*Assistant Examiner*—William E. Benston, Jr.
*Attorney, Agent, or Firm*—Dority & Manning

[57] ABSTRACT

A novel method for using domperidone, a dopamine receptor antagonist, for treating fescue toxicosis in animals is provided. Fescue toxicosis is caused by animals grazing on endophyte-infected fescue grass. Treatment of the animal with various dosages of domperidone results in effective management of the toxin. The domperidone treatments do not cause any substantial adverse behavioral or neurological side effects in the animal. Domperidone is a more effective treatment for fescue toxicosis than previously-known agents such a metoclopramide and sulpiride.

19 Claims, 7 Drawing Sheets

METHOD OF TREATING FESCUE TOXICOSIS WITH DOMPERIDONE

FIELD OF THE INVENTION

A process for treating and preventing fescue toxicosis in animals with domperidone is provided.

Background of the Invention

Tall fescue grass (*Festuca arundinacea*) is the pasture grass of choice in most humid, warm weather areas of the United States. Tall fescue is also used for various other purposes such as ground cover, parks, lawns, along waterways, and other areas where a quick-growing and durable grass is needed. Fescue is easily established, has a wide range of adaption, allows animals to graze for longer periods of time when used as pasture grass, is tolerant to abuse, is resistant to most pests, has good seed production, and exhibits a generally acceptable overall appearance.

Animals that feed on fescue, however, often suffer from fescue toxicosis. Fescue toxicosis is caused in animals by consuming endophyte-infected tall fescue. The particular endophyte is known as *Acremonium coenophialum*. Symptoms of fescue toxicosis in animals include (1) fescue foot, which is a gangrenous condition of the feet and/or tails, (2) summer syndrome, which is characterized by poor animal weight gains, intolerance to heat, excessive salivation, nervousness, dramatically reduced weaning weights, lower milk production, and a reduced pregnancy rate, and (3) bovine fat necrosis, which is characterized by hard fat masses and abdominal fat tissue deposits that cause poor digestion and calving problems. Other known symptoms include (4) agalactia, which is nonsecretion of milk following childbirth, (5) prolonged gestation, (6) weak or stillborn offspring, (7) retained placentas, (8) thickened placental tissue, (9) dystocia, and (10) rebreeding difficulties. In animals experiencing such symptoms, researches have observed decreased serum prolactin and progesterone levels.

As mentioned above, fungus growing on the fescue is the generally documented cause of fescue toxicosis in animals. Studies have shown that animal performance is greatly increased if they graze on low endophyte fescue as opposed to high endophyte-infected fescue. Generally, fescue toxicosis has been avoided in the past by shifting cattle from high to low endophyte-containing pastures.

Various dopamine antagonists have recently been examined as possible treatments for fescue toxicosis in both horses and cattle. Metoclopramide, a substituted benzamide related to sulpiride, has been shown to increase serum prolactin levels in animals consuming endophyte-infected tall fescue as shown in U.S. Pat. No. 4,880,632 to Lipham et al. Perphenazine, a phenothiazine derivative, has been used to treat fescue toxicosis induced by injection of bromocriptine.

Although both drugs offer some promise in treating the symptoms of fescue toxicosis, both drugs have the potential to produce various neurological side effects because they bind to central dopamine receptors. Metoclopramide has been shown to produce nervousness, listlessness, restlessness and depression in dogs, and can cause constipation with longterm use. Perphenazine is no longer used in quinine veterinary practice because it produces excitatory reactions in horses similar to those seen with chlorpromazine. Horses treated with chlorpromazine are generally sedated for the first few minutes after administration and then become unsteady, sinking backward on the hocks. Horses may then stumble and fall, followed by lunging and rearing. These types of side effects are undesirable for drugs used for longterm therapy in horses due to the high risk of injury to the horse and/or handler.

Additionally, as indicated in U.S. Pat. No. 4,880,632, various research has been conducted indicating that these and other $D_2$ specific dopamine antagonists may be employed as active agents for treating or preventing fescue toxicosis in animals. As described in U.S. Pat. No. 4,880,632, the $D_2$ specific antagonists that may be used to treat or prevent fescue toxicosis are those that cause minimal neurological and psychological adverse side affects in the animals. The patent describes and lists the above-mentioned substituted benzamides, such as metoclopramide, sulpiride, tiapride, and alizapride, as the preferred and available $D_2$ antagonists that may be used. Specifically, the U.S. Pat. No. 4,880,632 patent indicates that dopamine antagonists which exhibit psychotropic, neuroleptic or adverse neurological actions in animals must be avoided.

The patent also touts metoclopramide as being the preferred treatment for fescue toxicosis. Among the drugs listed in the U.S. Pat. No. 4,880,632 patent as being an ineffective treatment for fescue toxicosis due to its psychotropic or neuroleptic side effects is domperidone. Specifically, the U.S. Pat. No. 4,880,632 patent states that domperidone exhibits sufficiently adverse behavioral effects in animals that it would be eliminated from use in the prevention or treatment of fescue toxicosis. The patent states that this is not surprising because domperidone falls within compound groups known to have neuroleptic effects that were originally developed for anti-psychosis therapy, including phenothiazines, butyrophenones, and thioxanthenes. The U.S. Pat. No. 4,880,632 patent also states that domperidone is thought to be specific for $D_1$ receptors or a combination of $D_1$ and $D_2$ receptors. The patent fails to recite any examples or studies conducted by the Applicants in which domperidone was employed to treat fescue toxicosis.

Although various $D_2$ dopamine receptor antagonists have been employed to treat or prevent fescue toxicosis, domperidone has been viewed as an unacceptable drug for such treatment. Metoclopramide and sulpiride have been disclosed as treating fescue toxicosis, but domperidone has been considered as causing many behavioral and neurological side effects and, thus, has been avoided. The prior art does not suggest that domperidone could be employed as an effective agent in the treatment of fescue toxicosis. In fact, the prior art teaches that such treatments are discouraged and should be avoided. The present invention overcomes the shortcomings of the prior art in that a process for using domperidone to treat and prevent fescue toxicosis in animals without substantial side effects is employed.

SUMMARY OF THE INVENTION

It is an object of the present invention to provide a method for preventing and/or treating fescue toxicosis with domperidone.

It is a further object of the present invention to provide a $D_2$ dopamine receptor antagonist for treating fescue toxicosis in animals while avoiding substantial adverse behavioral and neurological side effects.

It is further another object of the present invention to provide a process for employing domperidone to effectively treat and/or prevent fescue toxicosis in farm animals grazing on endophyte-infected fescue grass.

Generally speaking, the present invention is directed to a method for treating and/or preventing fescue toxicosis caused by animals grazing on endophyte-infected fescue grass. The process employs the $D_2$ dopamine receptor antagonist domperidone in such treatments. Domperidone has heretofore been avoided in such fescue toxicosis treatment due to common knowledge that domperidone would produce adverse behavioral and neurological side effects in the animals. Broadly speaking, the present composition may be administered to farm animals, including cattle and mares, in varying doses to obtain an effective treatment for fescue toxicosis and prevention of the disease without creating the previously reported behavioral side effects.

DESCRIPTION OF PREFERRED EMBODIMENTS

Figure 1:
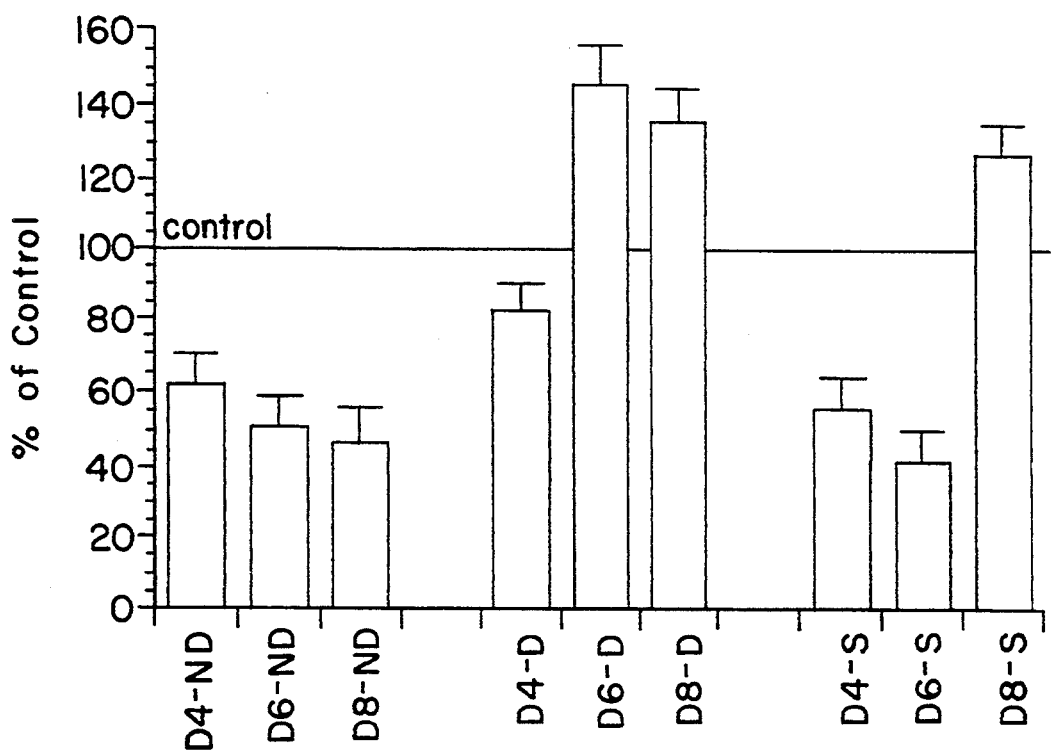
FIG. 1 is a bar graph illustrating the effect of dopamine, at $10^{-4}$ (D4), $10^{-4}$ (D6), and $10^{-8}$ (D8) M concentrations on prolactin secretion in the presence of no $D_2$ dopamine receptor antagonist (ND), domperidone (D) and sulpiride (S) as a percent of non-treated controls.

In studies directed to the present invention, the ability of domperidone to reverse adverse effects on prolactin treatment as compared to sulpiride was determined after attaining the following information: (1) the effects of ergovaline or loline on in vitro pituitary prolactin secretion; and (2) the activity of these alkaloids at the $D_2$ dopamine receptor using two selective $D_2$ dopamine receptor antagonists.

Recently, the ergopeptine (e.g., ergovaline) and loline-derivative (e.g. N-formyl loline and N-acetyl loline) alkaloids produced in endophyte-infected tall fescue have received much attention as possible causative agents of fescue toxicosis. One symptom consistently observed in animals consuming endophyte-infected tall fescue is hypoprolactinemea. Based on these observations, Examples 1-4 provide exemplary studies wherein a bioassay with rat anterior pituitaries was developed to study the effect of individual alkaloids produced by the endophyte on prolactin secretion in vitro; a cell culture bioassay was used to study the effects of ergovaline and loline on pituitary prolactin secretion in vitro; the site of action for these alkaloids was investigated indirectly using $D_2$ dopamine receptor antagonists; and, finally, domperidone was studied as to its efficacy to reverse the inhibitory effect of $\alpha$-ergocryptine on prolactin section in vitro and then compared to sulpiride's ability to do the same.

Example 1

Anterior pituitaries were collected from several 225 to 250 gram male Wistar rats. Anterior pituitary cells were dispersed with a trypsin enzymatic digestion and counted using a hemocytometer made by CMX of Houston. The trypan blue exclusion assay was used to determine pituitary cell viability.

Cells were plated into 24 well Falcon Primaria culture plates made by Becton Dickison of Lincoln Park, N.J., at a density of $1.0 \times 10^4$ live cells per well for Example 2 below and $1.0 \times 10^5$ live cells per well for Example 3 below. Cell cultures were incubated (37° C., 5% $CO_2$, 100% humidity) in culture medium until monolayer formation was achieved (approximately 7 days). Culture medium consisted of 90% Dulbecco's Modified Eagle's Medium ("DMEM") from Sigma of St. Louis, Miss., 7.5% horse serum from Sigma, 2.5% fetal calf serum from Sigma, 25 mM HEPES from Sigma, 2.5 μg/mL amphotericin B from Sigma, 100 μg/mL of penicillin from Sigma, 100 μg/mL of streptomycin from Sigma and 1.0 μg/mL of insulin. Monolayers were then exposed to their respective treatments.

Example 2

Treatments for this example included: (1) loline 2HCl supplied by R. G. Powell, USDA, ARS of Peoria, Ill.; (2) $\alpha$-ergocryptine from Sigma; (3) ergovaline from Sandoz Pharmaceuticals of Bezel, Switzerland; and (4) dopamine HCl from Sigma at three concentrations each of $10^{-4}$, $10^{-6}$, and $10^{-8}$M. Dopamine (a catecholamine) and $\alpha$-ergocryptine were used to verify that the control mechanisms for inhibitions of pituitary cell prolactin section were intact. Additionally, cells were exposed to domperidone obtained from Janssen Pharmacueticals of Belgium and sulpiride from Sigma at $10^{-6}$M concentrations each.

Dopamine HCl and loline 2HCl were solubilized with 70% ethanol. $\alpha$-Ergocryptine was solubilized in absolute ethanol and ergovaline was solubilized in acidified absolute ethanol (0.02N HCl). Domperidone and sulpiride were solubilized in 0.9% saline. The concentration of $D_2$ dopamine receptor antagonist (domperidone and sulpiride) or alkaloid carrier in treatment medium was 0.3%. All treatments were initially replicated four times. Controls consisted of four replicates each with no $D_2$ dopamine receptor antagonist/no alkaloid, domperidone/no alkaloid and sulpiride/no alkaloid. No carrier controls were performed because preliminary experiments had established that ethanol at 0.3% of the culture medium had no effect on prolactin secretion in vitro.

For one hour preceding treatment, exposure cells were incubated in 1 mL of DMEM to determine baseline pituitary prolactin secretion. After the pretreatment period, the medium was removed from the wells, spun (300 grams ×15 min), and placed into individual 12×75 mm glass tubes for storage at −20° C. until a prolactin (PRL) radioimmunoassay (RIA) could be performed.

Cells were then incubated for 3.5 hours in 1 mL of DMEM containing the particular $D_2$ dopamine receptor antagonist and alkaloid treatments. $D_2$ dopamine receptor antagonist treatments were placed into the appropriate wells at the beginning of the treatment period and incubated for 30 minutes. Immediately following incubation, the alkaloid treatments were added and the cells were again incubated for another 3 hours. Subsequently, the treatment medium was removed, spun (300 grams ×15 min) and placed into individually labeled 12×75 mm glass tubes for storage at −20° C. until assayed for prolactin.

Both baseline and treatment cell prolactin secretion were adjusted for milligrams of total cell protein in a well. Eight untreated wells were used to determine total cell protein in a well. Total cell protein per well was determined before and after the treatment period using a Coomassie dye binding assay bovine serum albumin as a standard obtained from a protein assay kit of Biorad of Richmond, Calif.

Example 3

Experimental procedures for Example 3 were performed as described above with respect to Example 2. Cells were pre-exposed to domperidone and sulpiride at concentrations of $10^{-5}$, $10^{-7}$, $10^{-8}$, $10^{-9}$ and $10^{-10}$M for 30 minutes prior to the addition of α-ergocryptine at $10^{-8}$M. Cells were then incubated an additional 3 hours. Treatments were made with domperidone and sulpiride at $10^{-5}$, $10^{-7}$, $10^{-8}$, $10^{-9}$, and $10^{-10}$M concentrations in competition with α-ergocryptine at $10^{-8}$M. Controls consisted of no carrier, drug carriers and α-ergocryptine, with and without drug carriers. α-Ergocryptine was solubilized in absolute ethanol; domperidone was solubilized in absolute ethanol; and sulpiride was solubilized in 5% glacial acetic acid. Carrier solutions for domperidone and sulpiride were altered in this example to facilitate the higher drug concentrations needed. Treatments were added as in Example 2 to restrict the carrier solution of each treatment to 0.3% of the medium.

Example 4

Prolactin radioimmunoassay was performed using materials and methods supplied by the *National Hormone and Pituitary Program* and the *National Institute of Diabetes and Digestive and Kidney Diseases*. Iodination of prolactin was performed by a lactoperoxidase method.

The results from Examples 2 and 3 were arranged as randomized block designs and analyzed by Analysis of Covariance. Blocks of the treatment replicates were fitted to remove variation due to location within a culture plate and each block represented one of four columns on a plate. The covariate, baseline prolactin secretion was fitted to remove well to well variation in prolactin secretion.

The analysis was performed in two stages. Initially, the model was run and the square root of the mean square error was used to identify outliers. Those data that were plus or minus two standard deviations away from the mean of the treatment were removed. The model was rerun to analyze for the main effects of $D_2$ dopamine receptor antagonists, alkaloid and $D_2$ dopamine receptor antagonist/ alkaloid interaction ($D_2$ dopamine receptor antagonist/alkaloid interaction only, for experiment 2). Least square means were calculated for each $D_2$ dopamine receptor antagonist/alkaloid treatment and expressed as a percent of the control. Orthoganol polynomial contrasts were used to fit the dose response curves of Example 3 and means separation was performed with a series of linear contrasts using Student's test. All analyses were performed using the GLM procedure of SAS.

Controls for Example 2 containing either domperidone ($10^{-6}$M) or sulpiride ($10^{-6}$M) stimulated prolactin secretion over that of the no $D_2$ dopamine receptor antagonist control. Prolactin values for controls were 853.9, plus or minus 75.0, 1267.4, plus or minus 73.0, and 1387.1, plus or minus 62.8 ng PRL/mL/mg protein for the no $D_2$ dopamine receptor antagonist control, domperidone control, and sulpiride control, respectively.

The main effects of the $D_2$ dopamine receptor antagonist/alkaloid interaction were significant. Those means were used to present the data shown in FIGS. 1-4. The designations and description of the data for each Figure are described above. In each run, domperidone and sulpiride were delivered at doses of $10^{-6}$M concentrations.

Figure 2:
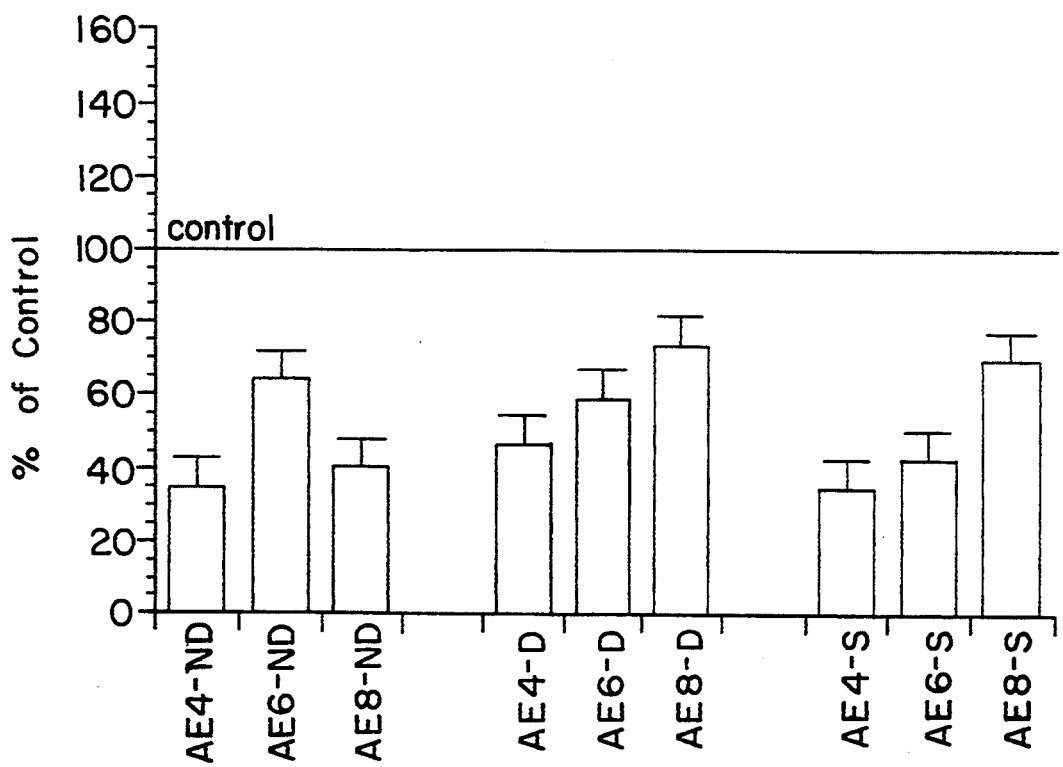
FIG. 2 is a bar graph illustrating the effect of $\alpha$-ergocryptine, at $10^{-4}$ (AE4), $10^{-6}$ (AE6), and $10^{-8}$ (AE8) M concentrations on prolactin secretion in the presence or absence of the antagonists identified in FIG. 1 as a percent of non-treated controls.
Figure 3:
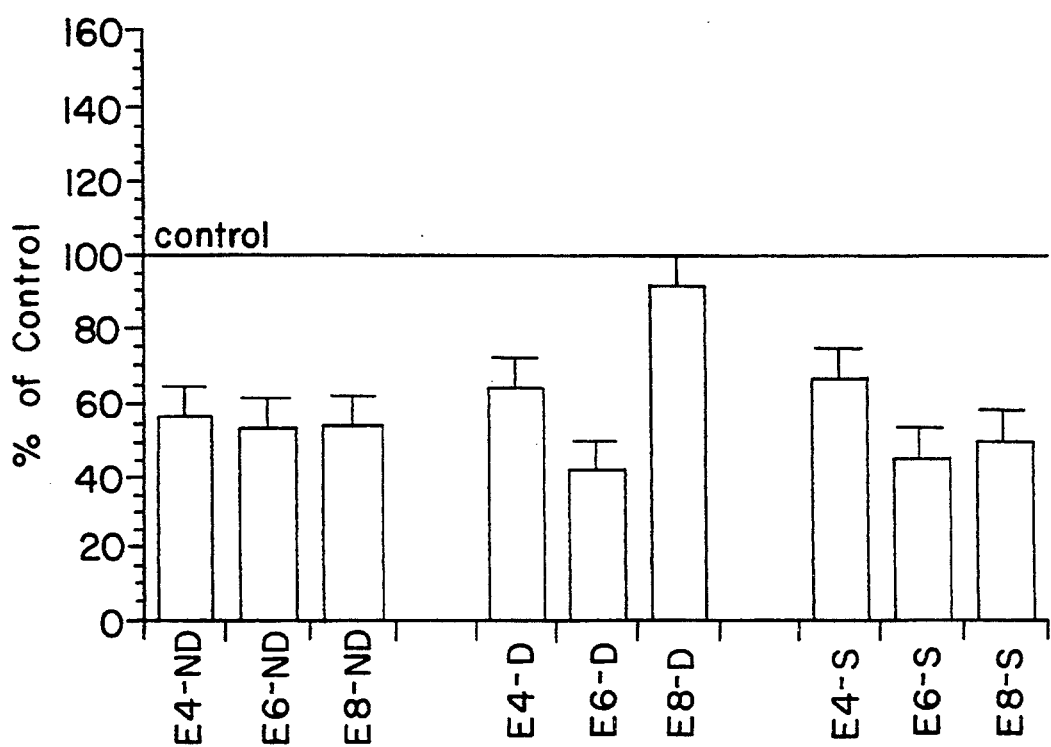
FIG. 3 is a bar graph illustrating the effect of ergovaline, at $10^{-4}$ (E4), $10^{-6}$ (E6), and $10^{-8}$ (E8) M concentrations on prolactin secretion in the presence or absence of the antagonists identified in FIGS. 1 and 2 as a percent of non-treated controls.
Figure 4:
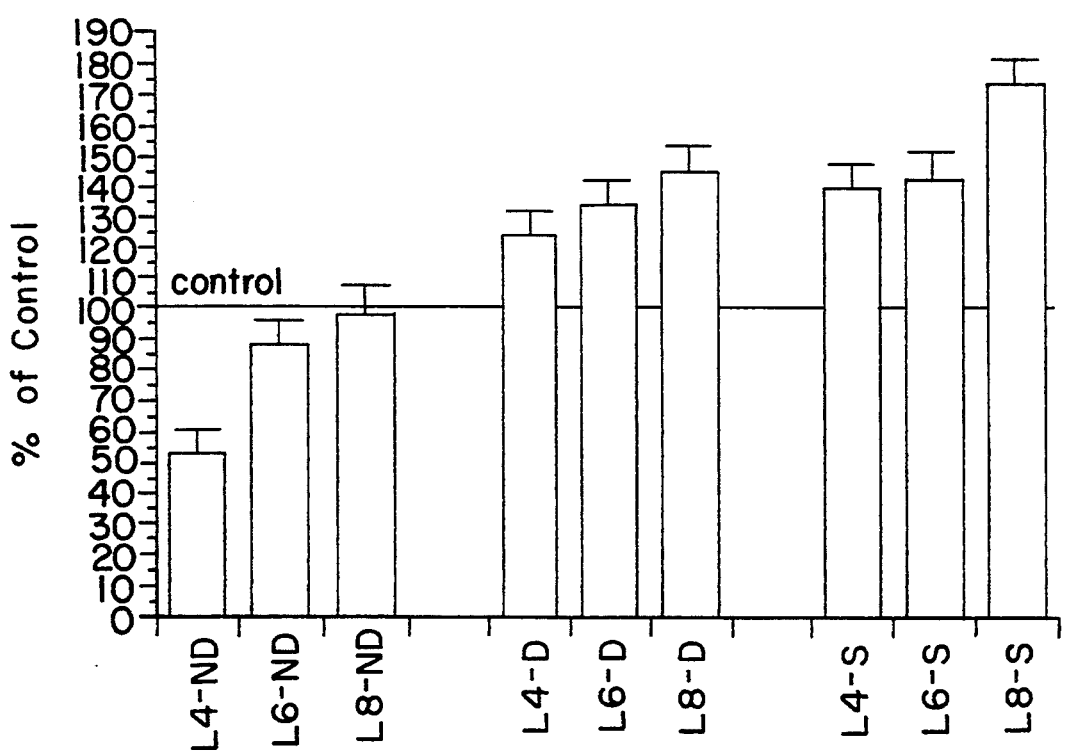
FIG. 4 is a bar graph illustrating the effect of loline, at $10^{-4}$ (L4), $10^{-6}$ (L6), and $10^{-8}$ (L8) M concentrations on prolactin secretion in the presence or absence of the antagonists identified in FIGS. 1, 2 and 3 as a percent of non-treated controls.
Figure 5:
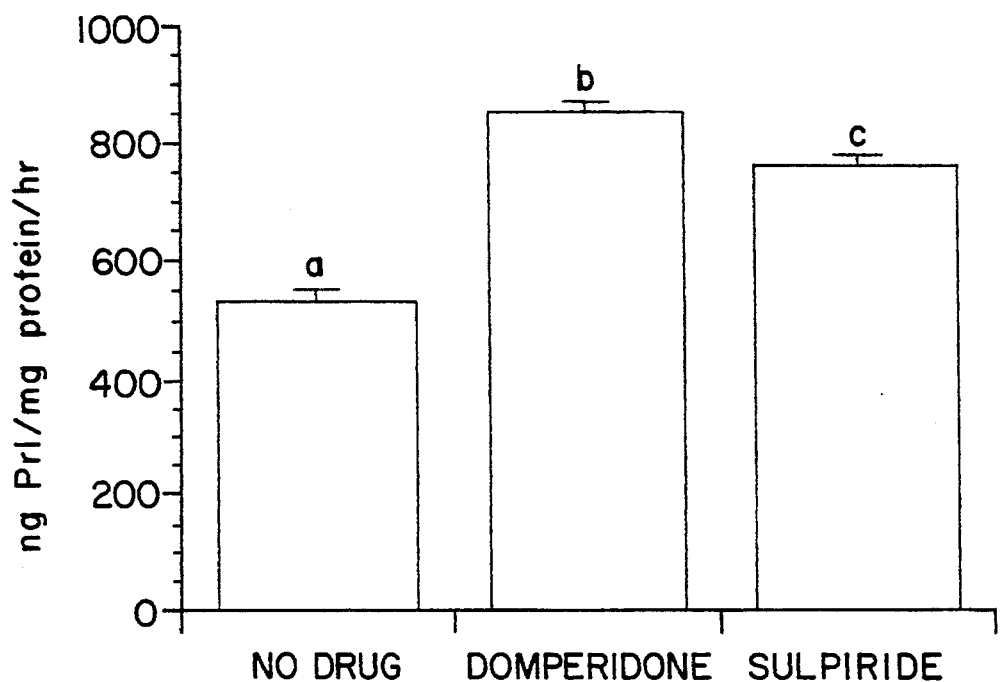
FIG. 5 is a bar graph illustrating the overall effect of domperidone and sulpiride on prolactin secretion, in vitro, across all alkaloid treatments.

As expected, both dopamine and α-ergocryptine suppressed prolactin secretion below that of the control across all three dosage levels, $10^{-4}$, $10^{-6}$ and $10^{-8}$M, as shown in FIGS. 1 and 2. No dose response effect of dopamine or α-ergocryptine on prolactin secretion was exhibited. It is possible that lower dosages or more pituitary cells were needed to create a dose response (i.e. receptors may have been saturated by the $10^{-8}$M concentration).

α-Ergocryptine, an ergopeptine alkaloid found in very low amounts in endophyte-infected tall fescue, was shown to inhibit prolactin secretion at the pituitary level. Therefore, the ability of dopamine and α-ergocryptine to suppress prolactin secretion in this in vitro system verifies that the cells were intact and responsive.

Determination of the potential toxicity of ergovaline is important considering its concentration of 0.3 to 2.8 μg/g of leaf sheath (greater than 80% of the total ergopeptine fraction), in endophyte-infected tall fescue. In Examples 1-4, ergovaline suppressed prolactin secretion in vitro at all concentrations tested in relation to the non-treated control and the magnitude of suppression was very similar to that of dopamine and α-ergocryptine. Ergovaline is a member of the same class of compounds, ergopeptines, as α-ergocryptine, ergocornine and ergotamine. All three ergopeptines have been shown to suppress pituitary prolactin secretion in vivo or in vitro.

As with α-ergocryptine and dopamine, there was no dose response effect of ergovaline on in vitro pituitary prolactin secretion. Cell numbers were speculated to be insufficient to elicit a dose response as described above. The presence of ergovaline in endophyte-infected tall fescue and its activity in vitro in suppressing prolactin secretion make a strong case for it being a causative agent of fescue toxicosis. Additionally, its chemical relationship to ergotamine, an ergopeptine known to cause vasoconstriction and dry gangrene of the extremities, as well reduced serum prolactin levels, only strengthens its position as a major component of the causative mechanism(s) of fescue toxicosis.

Loline suppressed prolactin secretion only at the highest concentration ($10^{-4}$M), thus, exhibiting a dose response effect not observed in the other alkaloid treatments. The presence of loline, a pyrrolizidine alkaloid and the parent compound of N-formyl and N-acetyl lolines, in endophyte-infected tall fescue has been reported. The dose response effect of loline seems to indicate that it has a much lower affinity for its target site or fewer binding sites than dopamine, $\alpha$-ergocryptine or ergovaline. Additionally, the ability of the $D_2$ dopamine receptor antagonist domperidone to reverse the effects of loline on prolactin secretion seems to indicate that the site of action for loline is the $D_2$ dopamine receptor.

Across all alkaloid treatments, domperidone was shown to be more efficient than sulpiride at antagonizing the prolactin suppressing effect of the alkaloids. Domperidone was able to completely reverse the effect of all three concentrations of dopamine on prolactin secretion. Sulpiride, however, was only able to reverse the effect of the $10^{-8}$M concentration of dopamine on prolactin secretion.

Both domperidone and sulpiride were able to partially reverse the effects of the lowest concentration ($10^{-8}$M) of $\alpha$-ergocryptine on prolactin secretion, but neither had an effect on prolactin secretion at the other treatment concentrations ($10^{-4}$, $10^{-6}$M) of $\alpha$-ergocryptine.

Sulpiride had no effect on suppression of prolactin by ergovaline. Domperidone, however, was able to completely reverse the suppression of prolactin secretion induced by the lowest concentration ($10^{-8}$M) of ergovaline. The ability of domperidone to antagonize the effect of ergovaline indirectly indicates that ergovaline is eliciting its effect on prolactin secretion through a $D_2$ dopamine receptor. Both domperidone and sulpiride were equally efficacious at reversing the effect of loline on prolactin section.

Figure 6:
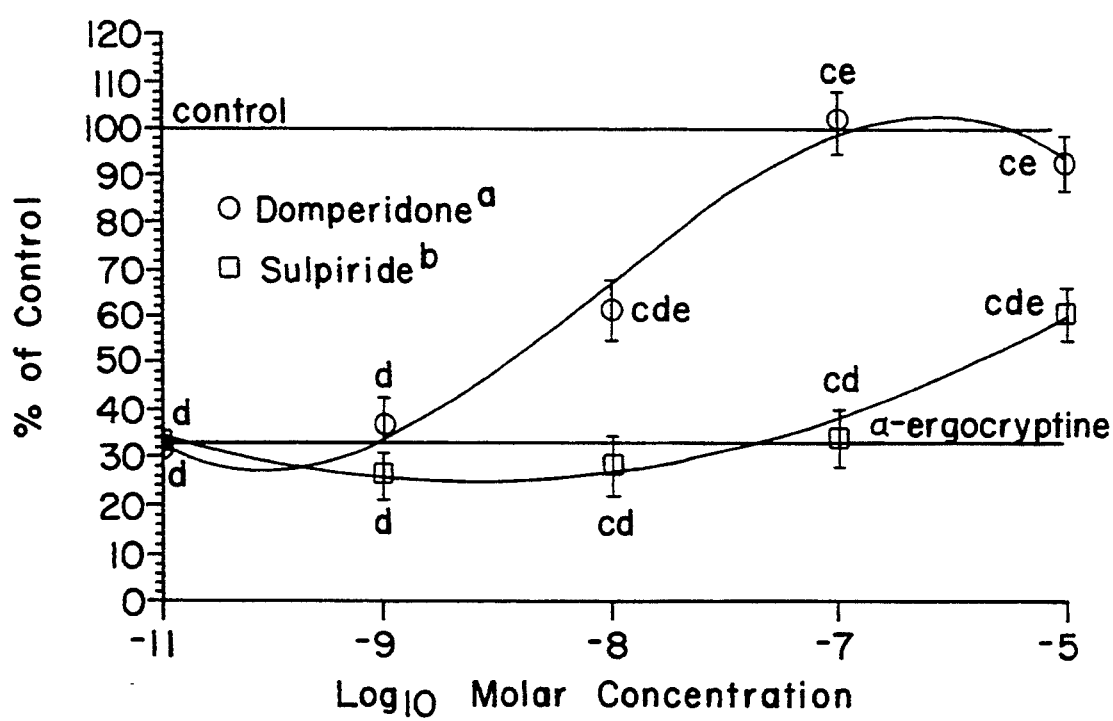
FIG. 6 is a graph illustrating the dose response relationships of domperidone and sulpiride on in vitro pituitary prolactin secretion in the presence of a $10^{-8}$ M concentration of $\alpha$-ergocryptine.

FIG. 6 shows the dose response relationships of domperidone and sulpiride on in vitro pituitary prolactin secretion in the presence of a $10^{-8}$M concentration of $\alpha$-ergocryptine. The dose response curve of domperidone had a significant cubit fit indicating that there was no added benefit to increasing doses of domperidone past $10^{-7}$M concentration. In contrast, the dose response curve of sulpiride had a significant quadratic fit and the dosages were not sufficiently concentrated to reach a plateau as was observed with domperidone. In fact, sulpiride was unable, even at the highest dose ($10^{-5}$M), to completely reverse the suppression of prolactin secretion caused by $\alpha$-ergocryptine ($10^{-8}$M) back to the control level. Domperidone, on the other hand, increased prolactin secretion above that of the $\alpha$-ergocryptine ($10^{-8}$M) control at doses of $10^{-8}$, $10^{-7}$, and $10^{-5}$M. Sulpiride was only able to increase prolactin secretion when given at $10^{-5}$M concentration. Accordingly, domperidone is a more potent $D_2$ receptor antagonist than sulpiride.

In summary, the results from the above Examples show that ergovaline reduced in vitro pituitary prolactin secretion by 40% or greater at $10^{-4}$, $10^{-6}$ and $10^{-8}$M concentrations. In contrast, loline reduced prolactin secretion only at the highest dosage given, $10^{-4}$M. Two standard dopamine agonists, dopamine and A-ergocryptine, were used to verify that the inhibitory control mechanisms of pituitary cell prolactin secretion were intact. Both reduced prolactin secretion by at least 40% for $10^{-4}$, $10^{-6}$ or $10^{-8}$M concentrations. The $D_2$ dopamine receptor antagonist domperidone at $10^{-6}$M was able to reverse the effect of loline on in vitro pituitary prolactin secretion and domperidone of $10^{-6}$M was able to reverse the effect of ergovaline at the lowest dosage ($10^{-8}$M). Domperidone was more effective in reversing the prolactin suppressing effect of the alkaloids than sulpiride. The dose response curve for domperidone indicated a threshold concentration, $10^{-7}$M, for reversal of $\alpha$-ergocryptine's effect on prolactin secretion. However, at similar concentrations of sulpiride, a threshold level was not obtained. These data indicate that both ergovaline and loline alkaloids are $D_2$ dopamine receptor agonists and that domperidone is a more potent drug for reversal of the alkaloids' hypoprolactinemic effects than sulpiride.

The greater efficacy of domperidone versus sulpiride to reverse the suppressing effect of a $\alpha$-ergocryptine on in vitro pituitary cell prolactin secretion may be explained by differences in chemical structure. Additionally, the different physiological distributions of sulpiride and domperidone in the animals' body may be useful in localizing the target tissues of tall fescue toxins in the animal. Domperidone, an investigational antiemetic distributed as Motilium in Europe, but not currently cleared for clinical use in the United States, is chemically unrelated to other antiemetics, such as butyrophenones, phenothiazines, and metoclopramide. Unlike other antiemetics (e.g., metaclopramide, haloperidol), domperidone does not cross the blood brain barrier. Therefore, central neurological side effects are not a concern when using domperidone as a treatment for fescue toxicosis. In contrast, sulpiride is a $D_2$ dopamine receptor antagonist of the same chemical class as metoclopramide, a drug that has been shown to be effective in reversing the hypoprolactinemea of fescue toxicosis in cattle. Both sulpiride and metoclopramide, however, cross the blood brain barrier.

The results from Examples 1-4 indicate that ergovaline and loline suppress prolactin secretion in a manner similar to that of dopamine and $\alpha$-ergocryptine, implicating these alkaloids as possible causative agents of fescue toxicosis. Further, the prolactin suppressing effect of these alkaloids was partially or totally reversed by the $D_2$ dopamine receptor antagonist domperidone. Therefore, treatment of the hypoprolactinemia of fescue toxicosis is possible using domperidone. Domperidone was shown to be a more potent antagonist than sulpiride, indicating that lower dosages of domperidone are required for treatment or prevention of fescue toxicosis. Further, the inability of domperidone to cross the blood brain barrier makes it a valuable tool for localizing the mechanisms of fescue toxicity to peripheral tissues, i.e., those outside the blood brain barrier. This inability to cross the blood brain barrier significantly reduces the chance of central neurological and adverse behavioral side effects when using domperidone.

Example 5

The effectiveness of domperidone was also evaluated as a treatment for equine fescue toxicosis comparative to sulpiride. As indicated above, gravid mares grazing on endophyte-infected tall fescue frequently exhibit one or more symptom of equine fescue toxicosis, including agalactia, prolonged gestation, weak or stillborn foals, retained placentas, thickened placental tissue, mild to severe dystocia and febfeeding difficulties. In addition, a failure of the foal to rotate into the proper position for delivery has been observed. Infected mares also exhibit decreased serum prolactin and progesterone levels.

In this Example, sixteen gravid mares (6 Quarter Horses and 10 Arabians) were assigned to one of three treatments by breed, expected foaling date and whether a maiden mare or having previously foaled. The treatments included: (1) control (no drugs); (2) 2.2 mg domperidone/kg body weight/day; and (3) 3.3 mg sulpiride/kg. Each treatment group contained at least one maiden mare. The control treatment group (C) contained one Quarter Horse and three Arabians, the domperidone treatment group (D) contained two Quarter Horses and four Arabians, and the sulpiride treatment group (S) contained three Quarter Horses and three Arabians.

Mares were pastured as a group on one of eight 1.0 hectare endophyte-infected tall fescue pastures with free access to complete vitamin and mineral salt blocks and fresh water throughout the study. The average infection level for endophyte-infected pastures was 95.0%, plus or minus 4.41%. Mares were rotated to a fresh pasture when canopy height in the pasture being grazed reached approximately 7.6 cm. Mares were vaccinated and dewormed according to normal herd health management practices for the Clemson University equine herd.

Weights and body condition scores were obtained on each mare at 28-day intervals until foaling. Mares and foals were weighed on the day of foaling. Prepartum weights were used to determine mare weight gain during gestation. Postpartum mare weights were used to determine foal weight as a percentage of mare weight. A subjective udder scoring system was developed and udder scores were assigned every five days, starting 30 days prior to each mare's expected foaling date and continuing until withdrawal from the infected pasture, then every two days until parturition if parturition had not already occurred. Blood samples were taken every five days, with the first sample taken one to two days prior to the start of treatment (30 days prior to expected foaling date). Samples were taken in the form of what is commonly called a "window", where one 20-ml sample is obtained by jugular venipuncture at the start of the window, then other samples are obtained every hour for four hours for a total of five samples per window. Samples were allowed to clot for 30 minutes at room temperature and then refrigerated at 4° C.. Samples were centrifuged within one hour after the last sample was drawn. Serum was drawn off and the five samples per window were combined into one sample. Aliquots were subsequently frozen at −10° C. until assayed for prolactin, progesterone and estradiol-17$\beta$ content.

A solid phase I$^{125}$ radioimmunoassay kit from Coat-a-Count, Diagnostic Products Corporation, Los Angeles, Calif., was used to measure serum progesterone. Serum estradiol-17$\beta$ was measured by the procedure of Henricks et al. 57 J. Anim. Science 247 (1983) with the modifications specified by Breuel et al. 30 Theriogenology 613 (1988). The procedure was further modified by using two 0.2 ml aliquots of HPLC grade methanol to remove the steroid from the columns as opposed to the two 0.5 ml aliquots used by Breuel. This change resulted in a decreased evaporation time of the methanol without affecting the amount of estradiol-17$\beta$ recovered from the columns. A heterologous equine-canine radioimmunoassay was used to measure serum prolactin.

The foaling date for each mare was calculated using the breed averages over a period of several years for the Clemson University herd. Due dates for Arabian mares were calculated using an average gestation length of 338 days. Quarter Horse due dates were based on an average gestation length of 342 days.

Administration of the treatments began 30 days prior to the expected foaling date for each mare. A corn and dried molasses mix was utilized as the carrier for the drug treatments. The mix contained 20% molasses to increase palatability of the treatments. Control mares received 454 gm/head/day of the carrier, with 20 ml of cider vinegar mixed into the grain. Domperidone mares received 454 gm/head/day of the carrier to which domperidone had been added at a level of 0.55 mg/kg body weight. During preliminary experimentation, it was determined that cider vinegar needed to be added to the mix to induce consumption by the mares of the apparently bitter-tasting sulpiride. Domperidone was dissolved in 5 ml of cider vinegar and mixed into the grain to facilitate even distribution of the compound. An additional 15 ml of cider vinegar was then added to encourage complete consumption of the ration.

Sulpiride administration was accomplished in the same manner as that of domperidone, but was administered at a level of 1.65 mg/kg body weight. Each mare was restrained by means of a halter and fed individually to insure consumption of the correct ration. Treatment continued until parturition occurred. Dose levels were increased to 2.2 mg domperidone/kg body weight and 3.3 mg sulpiride/kg body weight after the first mare on each drug foaled without adequate mammary development. Mares that had not foaled within seven days after their expected due date were moved to 1.0 hectare endophyte-free fescue pastures to minimize chances of death due to severe dystocia.

Data were analyzed by one-way ANOVA in a completely random design. Treatments served as main effects and individual mares served as experimental units. Within-mean square was used as the error term, and differences between means were tested using least significant difference. The General Linear Model of the Statistical Analysis System was used to perform all statistical analyses. The results are listed in Table 1 below.

TABLE 1

| Item | Control | Treatment[a] Domperidone | Sulpiride |
| --- | --- | --- | --- |
| Number of mares | 4 | 6 | 6 |
| Condition score | 6.31 ± .24 | 6.10 ± .20 | 6.27 ± .20 |
| Mare weight, kg | | | |
| Initial weight | 474.11 ± 35.00 | 478.73 ± 28.57 | 506.06 ± 28.57 |
| Final weight[b] | 460.26 ± 32.68 | 480.02 ± 26.69 | 506.51 ± 26.69 |
| Weight gain | −13.85 ± 6.07 | 1.28 ± 4.95 | .45 ± 4.95 |
| Number of live foals | 3 | 6 | 6 |
| Foal weight, kg | 41.32 ± 3.54 | 40.55 ± 2.89 | 42.45 ± 2.89 |

TABLE 1-continued

| Item | Control | Treatment[a] Domperidone | Sulpiride |
|---|---|---|---|
| As a percentage of mare weight, % | 10.08 ± .67 | 9.28 ± .55 | 9.50 ± .55 |
| Gestation length, days | 350.25 ± 4.17[c] | 338.67 ± 3.41[d] | 343.00 ± 3.41 |
| Number of days past expected foaling date | 11.25 ± 3.87[c] | −.67 ± 3.16[d] | 3.00 ± 3.16 |
| Retained placentas | 0 | 1 | 3 |
| Number of mares with milk at foaling | 3 | 5 | 4 |
| Number of mares rebred | 2 | 5 | 4 |

[a]Mean ± standard error.
[b]Last weight before parturition.
[c,d]Means within a row lacking a common superscript letter differ ($P < .05$).

Mare weights and body condition scores did not vary according to treatment. A trend, however, was observed towards weight loss in control mares as seen in Table 1. Mares consuming endophyte-infected fescue have been found to gain less than mares consuming endophyte-free fescue prior to parturition. Previous studies have shown that sheep and cattle gain less weight when grazing infected fescue when compared to their counterparts consuming endophyte-free fescue. There was no effect due to treatment on foal birth weights as seen in Table 1.

Domperidone-treated mares had shorter gestation lengths than control mares. No mare, however, was allowed to graze on infected fescue more than 7 days beyond her projected foaling date. The gestation lengths for the domperidone mares are comparable to those found for mares consuming fungus-free fescue that had an average gestation length of 333, plus or minus 5, days. Average gestation length is known to vary widely between horse breeds, and a slight difference between Arabians and Quarter Horses has been observed within the Clemson University herd (338 and 343 days, respectively). Domperidone-treated mares foaled much nearer to their expected foaling date than did control mares. While the gestation length for control mares was not as long as the gestation lengths observed when mares were allowed to go to term on infected fescue, it is comparable to the gestation length observed when mares were removed from infected pasture 10 days after their expected foaling dates. In addition, mares which foaled after removal from infected fescue required an average 10 days recovery time on fungus-free fescue before foaling.

No difference was observed between treatments for retained placentas. Control mares had no retained placentas, but this may have been due to the precautionary measures taken to minimize chances of mare death. It has been well documented that a retained placenta is one of the problems often encountered in fescue toxicosis. The domperidone mare that had retained her placenta foaled 7 days early. The mare was discovered immediately after delivering the foal and showed no signs of having experienced dystocia, a common cause of retained placenta in mares. The foal was weak and unable to stand unaided. The foal never suckled and died of a suspected congenital heart defect within 12 hours after birth. The lack of suckling stimulus to the mare may have contributed to the retention of the placenta by preventing the additional release of oxytocin which normally occurs upon the initiation of suckling. Oxytocin appears to be involved in hormonal control of placental expulsion. Mares that undergo oxytocin-induced parturition have prompt placental expulsion.

Three mares in the sulpiride group retained placentas. One of these mares foaled prior to the increase in dosage. The second sulpiride mare foaled 6 days after the dosage was increased. The third mare was on the higher dosage for the entire treatment period.

The numbers of mares with milk at foaling were similar among the treatments. The one control mare that foaled on infected pasture grass exhibited no signs of mammary development prior to parturition and was agalactic at parturition. One domperidone mare and one sulpiride mare had udder development that was insufficient to support lactation, and both foaled prior to the increase in dosage. The second sulpiride mare foaled 6 days following the increase in dosage. This mare was agalactic immediately following parturition but began secreting milk within 24 hours postpartum. All control mares that were relocated to a fungus-free pasture failed to show signs of mammary development until after relocation. Visible udder development occurred within three days after relocation and all three mares had milk at parturition.

Two control mares failed to conceive following the experiment. One of these mares foaled too late to be bred before the end of the breeding season. One domperidone-treated mare exhibited estrus but failed to conceive. One of the sulpiride mares which did not conceive had a history of lactational anestrus under normal (non-endophyte) conditions. The other sulpiride mare had a retained placenta and required treatment. Therefore, this mare exhibited only one estrus before the end of the breeding season and did not conceive during this estrus. Others had found earlier that mares which grazed on endophyte-infected fescue during pregnancy tended toward a lower rate of conception following removal from the infected fescue than did mares which grazed on fungus-free fescue during pregnancy.

Figure 7:
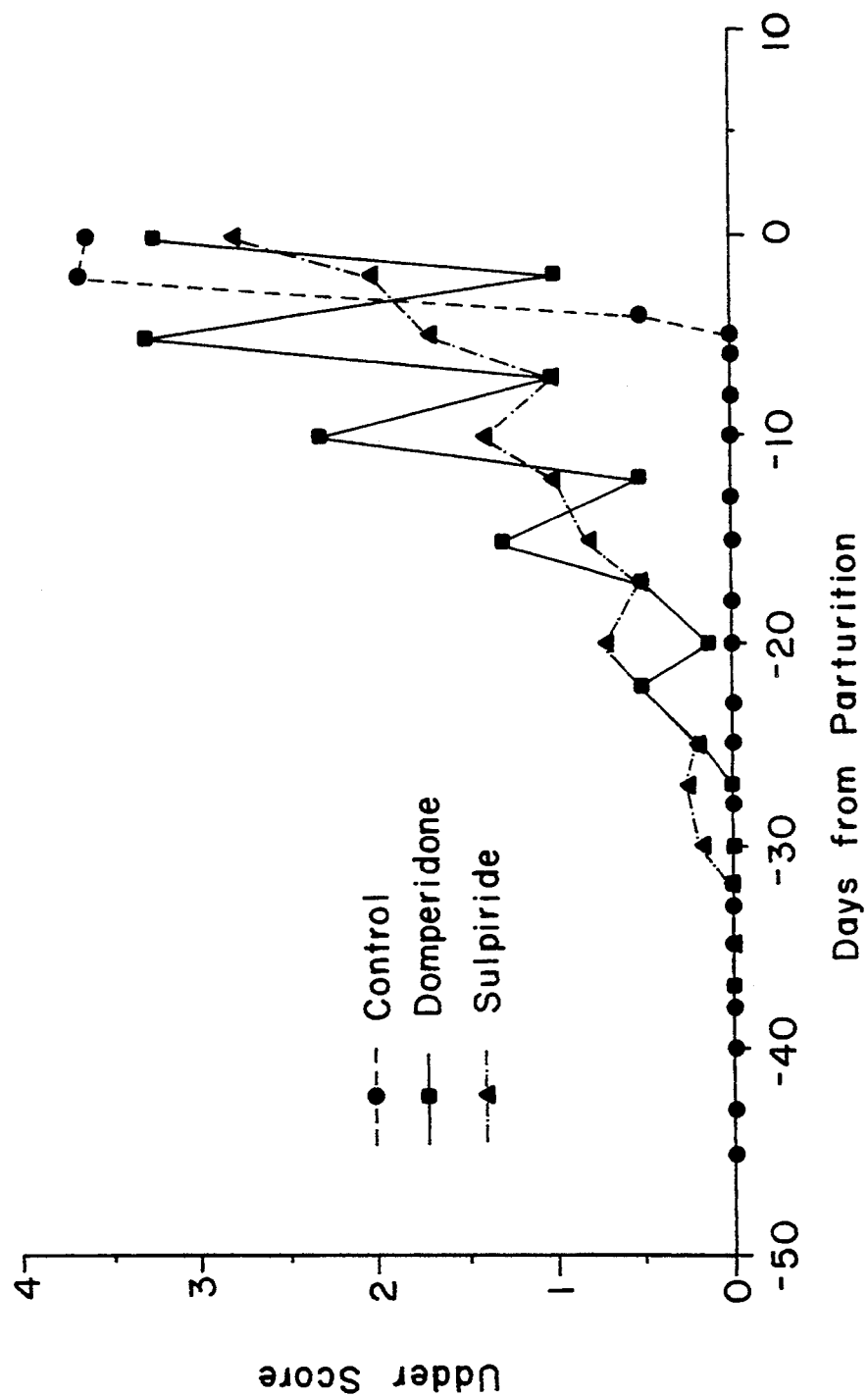
FIG. 7 is a graph illustrating the effects of domperidone and sulpiride treatments on mammary gland development.

FIG. 7 illustrates the effects of treatment on mammary gland development. Control mares showed no signs of udder development until after removal from endophyte-infected fescue. In contrast, domperidone and sulpiride mares began exhibiting palpable mammary development within 10 days after the start of treatment. Mammary gland scores were higher for domperidone and sulpiride versus control mares, but no significant difference between mammary scores for domperidone and sulpiride mares existed. The lack of mammary development in mares consuming endophyte-infected fescue has been well documented. FIG. 7 suggests that domperidone is an effective agent for ameliorating the effects of the endophytic toxins on mammary development.

Figure 8:
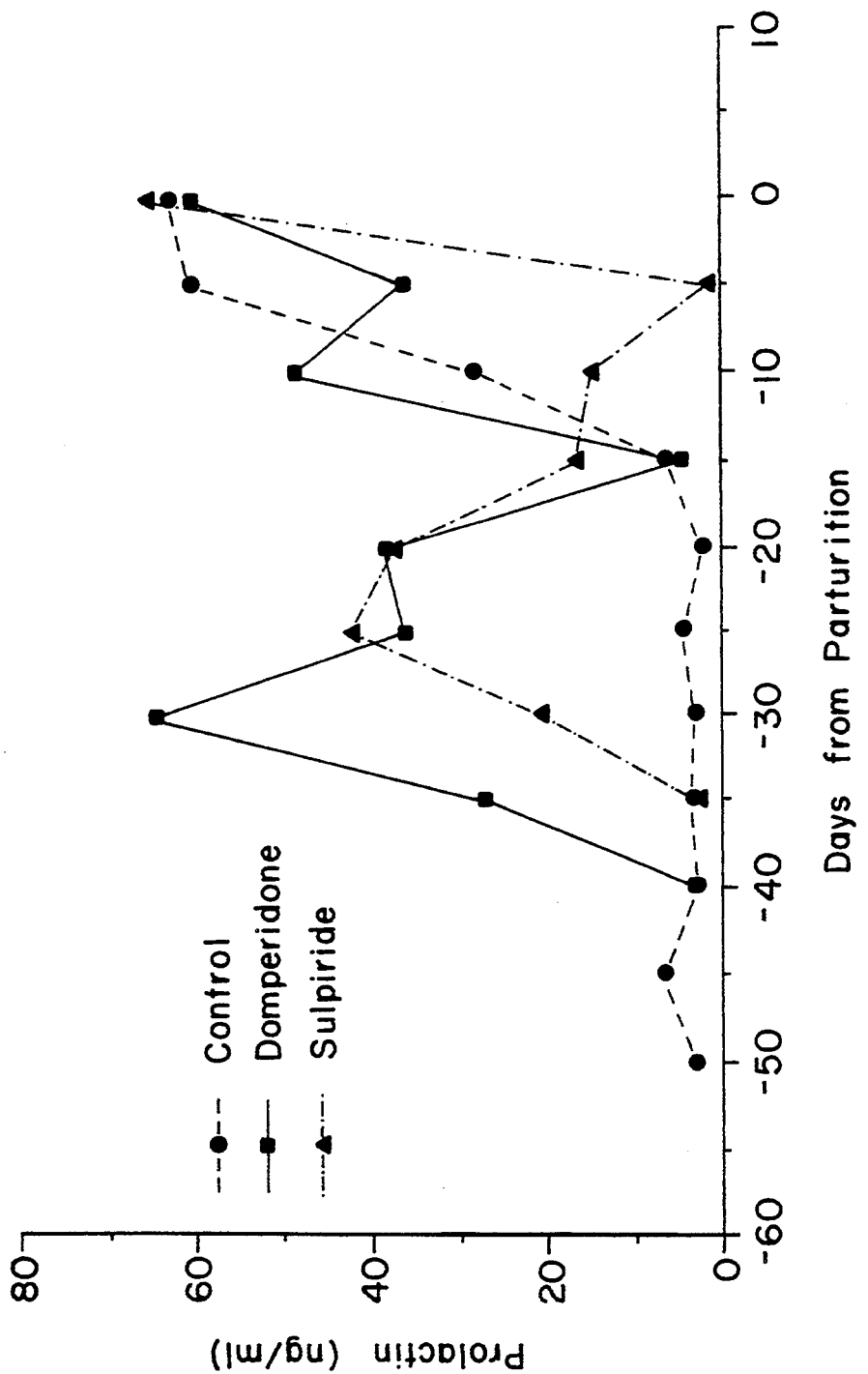
FIG. 8 is a graph illustrating the effects of domperidone and sulpiride treatments on prolactin secretion.

The effects of treatments on prolactin secretion are shown in FIG. 8. Serum prolactin was higher in domperidone and sulpiride mares than in control mares 10 and 15 days after treatment was initiated. Serum prolactin was higher in domperidone mares than control mares 20 and 30 days after the start of treatment. Prolactin levels for domperidone mares were similar to those of control mares 10 days before parturition. Prolactin levels tended to be higher for domperidone mares than sulpiride mares 5 days prior to parturition. Control mares had higher prolactin levels than sulpiride mares 5 days prior to parturition. There was no difference between treatments at parturition.

Serum prolactin levels in pregnant mares generally remained steady throughout pregnancy at approximately 7 ng/ml. Also, recent research shows that prolactin levels in normal mares begin to increase greatly around 5 days prior to parturition, corresponding to the increase in production of the various milk components in the mare. However, serum prolactin levels remained below 5 ng/ml in control mares until their removal from endophyte-infected tall fescue 9.33, plus or minus 2.49, days prior to parturition. The control mare that foaled on endophyte-infected tall fescue had a serum prolactin level of 1.15 ng/ml in the last blood sample prior to parturition. The three control mares that were removed from the infected tall fescue showed a rapid increase in prolactin levels following removal from infected tall fescue.

Figure 9:
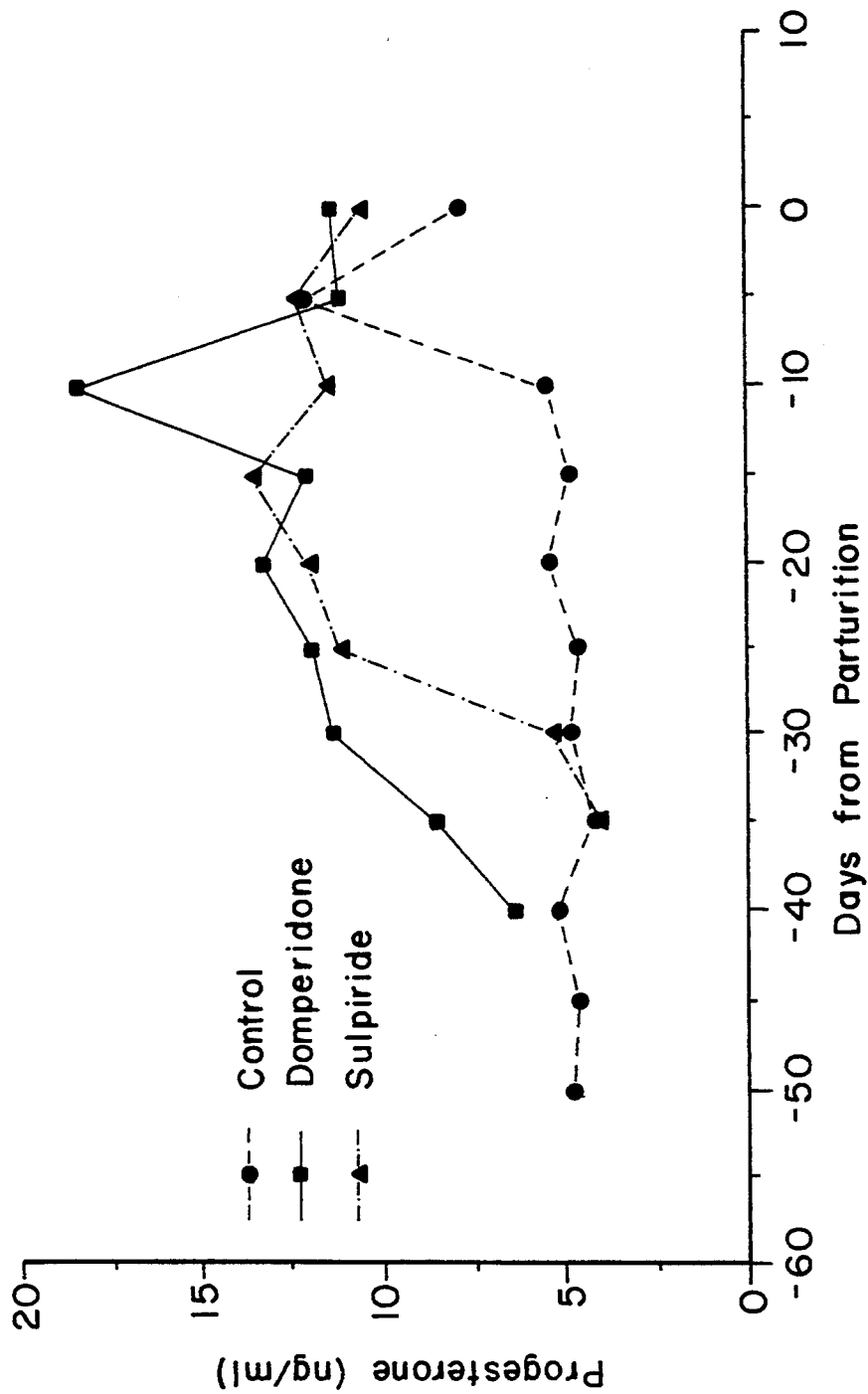
FIG. 9 is a graph illustrating the effects of domperidone and sulpiride treatments on serum progesterone levels.

FIG. 9 illustrates the effects of treatments on serum progesterone levels. Serum progesterone levels were higher in domperidone and sulpiride mares than in control mares 10, 15, 20, 25, and 30 days after the start of treatment. Serum progesterone levels were higher in domperidone mares than sulpiride mares 30 days after initiation of treatment (−10 and −5 days from parturition for domperidone and sulpiride mares, respectively). Serum progesterone levels were similar among treatments 35 days after the initiation of treatment (−5, 0 and −15 days from parturition for domperidone, sulpiride and control mares, respectively). Serum progesterone levels were similar for all treatments at parturition. Progesterone levels in control mares remained steady until removal from infected fescue and then began to increase. The increase in serum progesterone in control mares beginning at 10 days from parturition was probably associated with the removal of these mares from endophyte-infected pasture 9.33, plus or minus 2.45, days prepartum.

Mares consuming endophyte-infected fescue have been shown to have decreased serum progesterone levels. Progesterone in pregnant mares is low from about day 160 of gestation to about day 280, then gradually increases until parturition. The results shown in FIG. 9 suggest that domperidone administration creates a more normal progesterone profile for mares consuming infected fescue without domperidone therapy.

Figure 10:
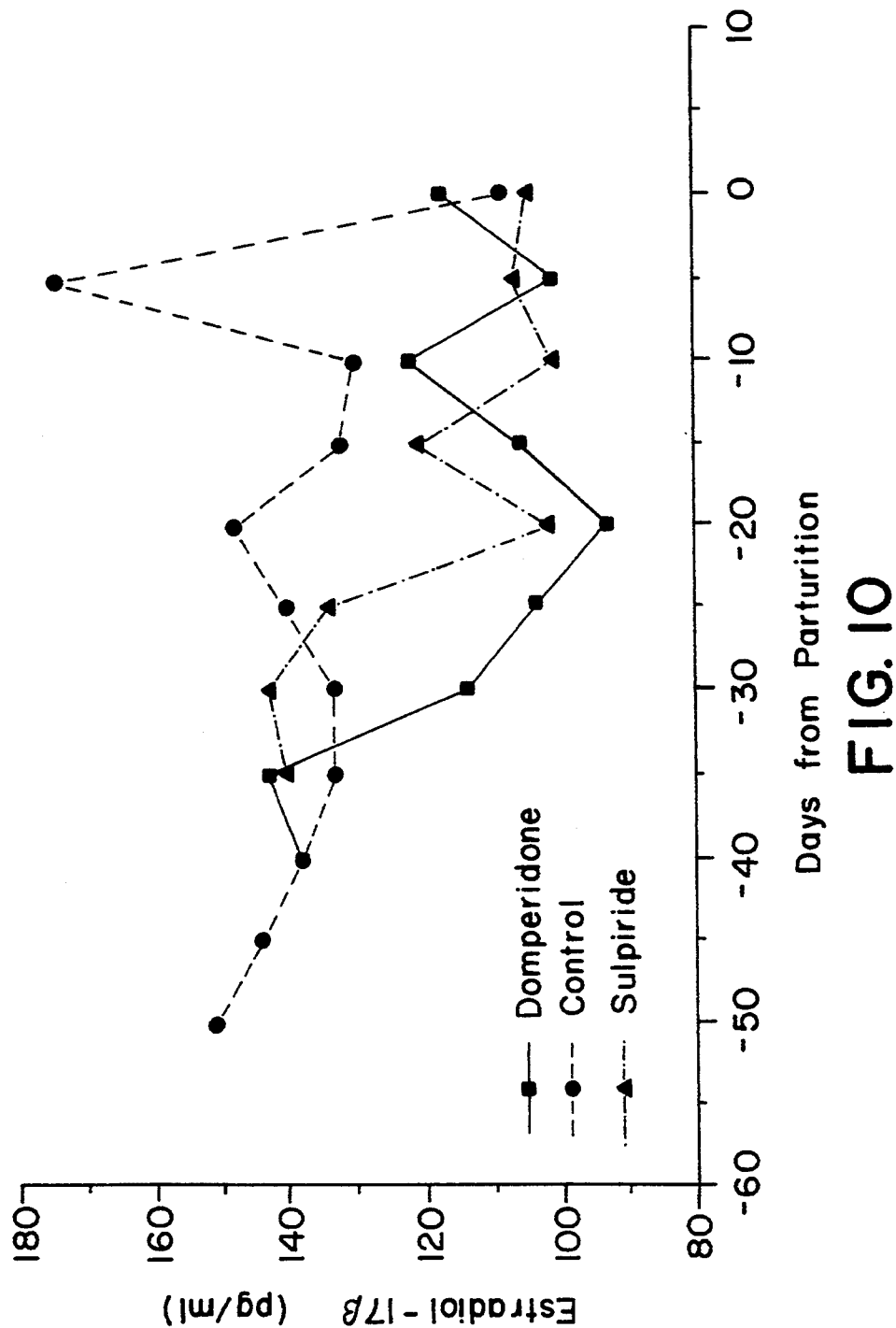
FIG. 10 is a graph illustrating the effects of domperidone and sulpiride treatments on serum estradiol-$17\beta$ levels.

The effect of treatment on serum estradiol-17β levels is shown in FIG. 10. Domperidone- and sulpiride-treated mares had lower serum estradiol levels than control mares. Estrogen levels in pregnant mares peak around day 200 of gestation then begin to steadily decrease from day 240 to parturition. FIG. 10 illustrates that estradiol-17β in control mares remained steady until the mares were removed from endophyte-infected fescue, then dropped rapidly, possibly in response to the absence of toxins in the diet. In contrast, estradiol-17β began to drop in both domperidone and sulpiride mares several days after therapy. The current data suggests that estradiol-17β is elevated as a result of endophyte consumption, and the treatment with domperidone or sulpiride will restore the secretion pattern of this hormone to near normal levels.

In contrast to other dopamine antagonists, such as metoclopramide and perphenazine, domperidone does not cross the blood-brain barrier and, therefore, does not produce central nervous system side effects. No neurological side effects were observed in any of the groups treated with domperidone during these studies.

Example 6

Twenty gravid mares (10 Quarter Horses and 10 Arabians) were assigned by breed and expected foaling date to one of five treatments: (1) endophyte-free (E-); (2) 1.10 mg domperidone/kg body weight/day (D1); (3) 1.65 mg domperidone/kg body weight per day (D2); (4) 2.20 mg domperidone/kg body weight per day (D3); and (5) endophyte-infected control (E+) in a randomized block design. E- mares grazed on 0.0% endophyte-infected pastures while all other mares grazed on 95.0%, plus or minus 4.41%, endophyte-infected pastures. All mares were allowed free access to complete mineral and vitamin blocks and water throughout the study.

The above-described treatments were administered orally in 454 grams of an 80% corn/20% dried molasses mixture daily, beginning 30 days prior to their expected foaling date. Mares were weighed and assigned body condition scores at 20 day intervals. Blood windows were taken at 5 day intervals beginning 30 days prior to expected foaling dates to determine effects of treatment on serum levels of prolactin, progesterone and estradiol-17β. A single postprandial blood sample was taken daily for the first five days of treatment to asses the initial effects of treatment on serum hormones. D3 mares had a greater incidence of retained placentas than E+, E− and D1 mares. Foal weights were higher for D1 mares than D2 and D3 mares. Gestation lengths were longer for E+ mares than E−, D1, D2 and D3 mares. The results of this Examples shows that a 1.10 milligram dose of domperidone/kg body weight/day is an effective level for treatment of equine fescue toxicosis.

Example 7

Twenty beef steers averaging approximately 750 pounds were employed to determine the effectiveness of domperidone in treating symptoms of fescue toxicosis in cattle. All steers were given free access to endophyte-infected hay and were also fed one pound/head/day of endophyte-infected fescue seed to further increase the intake of toxins. Then ten of the steers were injected subcutaneously daily with 75 mg of domperidone in a carrier and the other ten steers were injected daily with only the carrier.

Growing cattle consuming endophyte-infected grass, hay or seed were found to gain at a slower rate than cattle consuming uninfected grass, hay, or seed. The average daily gain of steers for the duration of this Example over three months was 1.57 pounds/head/day for control steers and 1.71 pounds/head/day for domperidone-treated steers. This represents a 9% increase in gain performance for domperidone treated steers.

Domperidone-treated steers appeared more healthy than control steers. Control steers created water bogs in the barn area and tried to lay in them to cool themselves and, therefore, had mud and manure covering their bodies. Domperidone-treated steers did not have this appearance. Control steers were sometimes seen coughing, were very slow in walking and exhibited some slobbering. The eyes of the control steers appeared more dull and the cattle had a general listless appearance. The domperidone steers appeared normal and healthy. Feedlot buyers report that steers and heifers coming from fescue growing areas of the country appear sick upon arrival at the feedlot and frequently require more medication and treatment upon arrival.

Domperidone is an effective treatment for fescue toxicosis and is more effective than sulpiride. In vivo, mares treated with domperidone had shorter gestation lengths, foaled closer to the expected foaling dates, exhibited better mammary development, had higher serum prolactin and progesterone levels and had lower serum estradiol-17β levels than control mares. Sulpiride was less effective than domperidone at ameliorating the effects of the endophytic toxins on hormone secretion. In addition, the effects on steers indicate toxicosis control with domperidone.

In delivering the effective dosages of domperidone to the animals, various vehicles may be used, including a feed or feed supplement material as the carrier, injection with a suitable carrier, administration orally alone or encapsulated, and in an implantable matrix. Additionally, domperidone may be added to a salt or mineral blocks during casting or mixed directly into seed. Various other administration techniques well known in the art may be employed. The present invention is not limited to any particular vehicle.

It will be understood that the invention is not limited to any specific parameters, amounts, or processes described herein, and that any method employing agents equivalent to those described falls within the scope of the present invention. It will be understood that while the form of the invention shown and described herein constitutes a preferred embodiment of the invention, it is not intended to illustrate all possible forms of the invention. The words used are words of description rather than of limitation. Various changes and variations may be made to the present invention without departing from the spirit and the scope of the following claims.

What is claimed is:

1. A method for treating or preventing fescue toxicosis in an animal comprising:
   administration of a composition to said animal wherein said composition contains an active agent comprising domperidone at a pharmaceutically effective dosage to treat or prevent fescue toxicosis in said animal and wherein said method treats or prevents fescue toxicosis with minimal neurological and psychological adverse side effects in said animal.

2. The method of claim 1 wherein said animal comprises a steer.

3. The method of claim 1 wherein said animal comprises a horse.

4. The method of claim 1 wherein said domperidone is administered orally to said animal.

5. The method of claim 1 wherein said administration comprises the further step of mixing a pharmaceutically effective dose of said domperidone with feed or feed supplement material.

6. A method of treating or preventing fescue toxicosis in an animal comprising the step of administering a pharmaceutically effective dosage of domperidone to said animal.

7. The method of claim 6 wherein said domperidone is administered by subcutaneous injection into the body of said animal.

8. The method of claim 6 wherein said domperidone is administered orally to said animal in a suitable carrier.

9. The method of claim 6 wherein said domperidone is administered through a time-released implant within the body of said animal.

10. The method of claim 1, wherein said composition comprises a pharmaceutically acceptable carrier for said domperidone.

11. The method of claim 10, wherein said composition is injected subcutaneously into said animal.

12. The method of claim 1, wherein said animal is a grazing animal.

13. The method of claim 6, wherein said animal is a grazing animal.

14. A method of treating an animal that has ingested ergopeptine and loline-derivative alkaloids, said method comprising the step of administering a pharmaceutically effective dosage of domperidone to said animal to combat any adverse effects to said animal caused by said alkaloids.

15. The method of claim 14, wherein said administration comprises the further step of mixing a pharmaceutically effective dose of said domperidone with feed or feed supplement material.

16. The method of claim 14, wherein said domperidone is injected subcutaneously into said animal.

17. An animal food comprising a composition for treating or preventing fescue toxicosis in an animal, said composition comprising domperidone at a pharmaceutically effective dosage to treat or prevent fescue toxicosis in said animal.

18. The animal food of claim 17, wherein said food comprises a mix of corn and dried molasses.

19. The animal food of claim 18 further comprising cider vinegar.

* * * * *